(12) United States Patent
Schwager

(10) Patent No.: US 6,206,834 B1
(45) Date of Patent: *Mar. 27, 2001

(54) STIFFENED HOLLOW VASCULAR DEVICE

(75) Inventor: Michael Schwager, Wintherthur (CH)

(73) Assignee: Schneider (Europe) A.G., Bulach (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/949,538

(22) Filed: Oct. 14, 1997

Related U.S. Application Data

(63) Continuation of application No. 08/949,538, filed on Oct. 14, 1997, which is a continuation of application No. 08/581,416, filed on Dec. 29, 1995, now abandoned.

(30) Foreign Application Priority Data

Jun. 29, 1995 (EP) .................................................. 95110117

(51) Int. Cl.[7] ........................................................ A61B 5/02
(52) U.S. Cl. ......................... 600/485; 600/486; 600/561; 600/585
(58) Field of Search ................................... 600/485, 486, 600/488, 585, 561, 368; 604/280, 282

(56) References Cited

U.S. PATENT DOCUMENTS

| Re. 33,911 | * | 5/1992 | Samson et al. ...................... 128/772 |
|---|---|---|---|
| 4,003,369 | | 1/1977 | Heilman et al. . |
| 4,080,706 | | 3/1978 | Heilman et al. ........................ 29/173 |
| 4,413,989 | | 11/1983 | Schjeldahl et al. .................... 604/96 |
| 4,456,000 | | 6/1984 | Schjeldahl et al. . |
| 4,545,389 | | 10/1985 | Schaberg et al. . |
| 4,573,966 | | 3/1986 | Weikl et al. ............................ 604/53 |
| 4,610,662 | | 9/1986 | Weikl et al. ............................ 604/53 |
| 4,646,742 | | 3/1987 | Packard et al. . |
| 4,724,846 | | 2/1988 | Evans, III . |
| 4,757,194 | | 7/1988 | Simms . |
| 4,779,628 | | 10/1988 | Machek . |
| 4,787,388 | | 11/1988 | Hofmann . |
| 4,811,737 | | 3/1989 | Rydell . |
| 4,821,735 | | 4/1989 | Goor et al. . |
| 4,844,092 | | 7/1989 | Rydell et al. . |
| 4,846,191 | | 7/1989 | Brockway et al. . |
| 4,854,330 | | 8/1989 | Evans, III et al. . |
| 4,895,168 | * | 1/1990 | Machek ................................ 128/772 |
| 4,901,731 | | 2/1990 | Millar . |
| 4,928,693 | | 5/1990 | Goodin et al. . |
| 4,953,553 | | 9/1990 | Tremulis ............................... 128/637 |
| 4,964,409 | | 10/1990 | Tremulis ............................... 128/657 |
| 4,986,830 | | 1/1991 | Owens et al. ......................... 606/194 |
| 5,040,543 | * | 8/1991 | Badera et al. ......................... 600/585 |
| 5,050,606 | | 9/1991 | Tremulis ............................... 128/637 |
| 5,063,935 | | 11/1991 | Gambale .............................. 128/657 |
| 5,063,936 | | 11/1991 | Sato et al. . |

(List continued on next page.)

FOREIGN PATENT DOCUMENTS

| 0313836A3 | 5/1989 | (EP) . |
|---|---|---|
| 0383159A1 | 8/1990 | (EP) . |
| 0419277A1 | 3/1991 | (EP) . |
| 0475773A1 | 3/1992 | (EP) . |
| 0475773 | * 3/1992 | (EP) ................................ A61B/8/12 |

*Primary Examiner*—Linda C. M. Dvorak
*Assistant Examiner*—R Kearney
(74) *Attorney, Agent, or Firm*—Todd P. Messal

(57) ABSTRACT

The medical appliance has an elongated tubular shaft with a lumen extending therethrough and slots in the distal area for pressure medium entry into the lumen. A stiffening means in the form of an independent wire extends through the lumen with its proximal area extending proximally of the shaft. The proximal area of shaft is affixed to a luer-lock comprising a housing with an inner cavity and a distal end forming a muff fixedly and tightly sealed on the proximal end of the shaft.

20 Claims, 3 Drawing Sheets

U.S. PATENT DOCUMENTS

| | | | |
|---|---|---|---|
| 5,088,991 | 2/1992 | Weldon | 604/280 |
| 5,098,381 | 3/1992 | Schneider | 604/96 |
| 5,127,917 | 7/1992 | Niederhauser et al. | 606/191 |
| 5,163,906 | 11/1992 | Ahmadi | 604/101 |
| 5,209,729 | 5/1993 | Hofmann | 604/96 |
| 5,232,445 | 8/1993 | Bonzel | 604/96 |
| 5,270,086 | 12/1993 | Hamlin | 428/35.2 |
| 5,281,203 * | 1/1994 | Ressemann | 128/772 |
| 5,295,961 | 3/1994 | Niederhauser et al. | 604/96 |
| 5,306,247 | 4/1994 | Pfenninger | 604/96 |
| 5,364,357 | 11/1994 | Aase | 604/96 |
| 5,368,567 | 11/1994 | Lee | 604/102 |
| 5,383,855 | 1/1995 | Nicholson et al. . | |
| 5,404,886 | 4/1995 | Vance . | |
| 5,404,887 * | 4/1995 | Prather | 128/772 |
| 5,413,581 | 5/1995 | Goy | 606/194 |
| 5,423,742 | 6/1995 | Theron | 604/28 |
| 5,425,712 | 6/1995 | Goodin | 604/96 |
| 5,429,139 | 7/1995 | Sauter . | |
| 5,450,853 | 9/1995 | Hastings et al. . | |
| 5,496,271 | 3/1996 | Burton et al. | 604/54 |
| 5,501,759 | 3/1996 | Forman | 156/272.8 |
| 5,505,699 | 4/1996 | Forman et al. | 604/96 |
| 5,507,301 * | 4/1996 | Wasicek et al. | 128/772 |
| 5,511,559 | 4/1996 | Vance . | |
| 5,527,298 | 6/1996 | Vance et al. | 604/280 |
| 5,569,197 | 10/1996 | Helmus et al. | 604/96 |
| 5,587,125 | 12/1996 | Roychowdhury | 264/515 |
| 5,605,163 | 2/1997 | Hani . | |
| 5,617,875 | 4/1997 | Schwager . | |
| 5,628,755 | 5/1997 | Heller et al. | 606/108 |
| 5,769,796 * | 6/1998 | Palermo et al. | 600/585 |
| B1 4,762,129 | 7/1991 | Bonzel . | |

* cited by examiner

STIFFENED HOLLOW VASCULAR DEVICE

This is a continuation of application Ser. No. 08/949,538, filed Oct. 14, 1997, which is a continuation of Ser. No. 08/581,416 filed Dec. 29, 1995, now abandoned.

BACKGROUND OF THE INVENTION

This invention relates to a medical appliance for pressure measurement in a blood vessel, comprising an elongated flexible shaft with a proximal area and a distal area, a lumen extending through the shaft from the proximal area to the distal area thereof, aperture means in the distal area of the shaft for the entry of a pressure medium into the lumen, and stiffening means in the lumen for stiffening shaft portions with full available shaft stiffness.

The monitoring of fluid pressures during intravascular procedures such as angioplasty gives valuable information to the cardiologist to assess both coronary myocardial flow reserve and collateral blood flow.

Attempts have been made to develop hollow guide wire systems which allow for the measurement of the fluid pressure at the distal end of a catheter from the proximal end thereof. The problem with that kind of pressure measuring guide wire is to provide an uninterrupted lumen throughout the shaft which has to be highly flexible to conform with tortuous pathways of the blood vessels; and simultaneously, the shaft must have an acceptably high stiffness to have pushability and assure torque transmission as well as it must have a very good kink resistance to avoid the risk of constrictions which could result in modification of the advance of pressure waves through the lumen.

For example U.S. Pat. No. 5,050,606 describes a flexible guiding member which can be utilized for monitoring of fluid pressure during intravascular procedures, or which can be utilized for directing inflation fluid to the interior of a dilatation balloon during angioplasty procedures. This guiding member has a main elongated tubular shaft with an inner lumen extending therethrough to an axial port in the distal end thereof. A core member is secured within the inner lumen and extends out of the distal end of the shaft. A tubular extension is disposed about the portion of the core member which extends out of the shaft and is secured at its proximal end to the distal end of the shaft; its distal end is provided with pressure monitoring ports. The proximal end of the core is secured within the distal end of the shaft by means of a weldment and this core wire has a cross-sectional area substantially less than the smallest transverse cross-sectional area of the inner lumen of the shaft. When the system is utilized in an independent guide wire configuration, the distal end of the tubular extension is bonded to the core member extending therethrough and also to a flexible body such as a helical coil which is disposed about and secured to the portion of the core which extends out of the distal end of the tubular extension. When the system is utilized in a so-called low profile steerable dilatation catheter configuration, an inflatable balloon is secured by its proximal end to the distal end of the tubular extension, and the distal end of the balloon is sealed about the portion of the core which extends out of the distal end of the tubular extension; the proximal end of the balloon is also bonded to the core. The tubular shaft is stiff and the tubular extension is diametrically relatively rigid to prevent kinking but it is longitudinally more flexible than the shaft because it is this distal portion of the system which must be advanced out of the guiding catheter into the patient's tortuous vasculature. The proximal end of the tubular shaft may be provided with a removable adapter to direct inflation fluid into the inner lumen thereof. U.S. Pat. No. 4,964,409 describes the same device as U.S. Pat. No. 5,050,606 which is referred to hereinbefore.

European Patent Application 0 313 836 shows a pressure monitoring guide wire having a tubular shaft with an axially extending lumen. A tubular member extends axially from the distal end of the shaft in axial alignment with the lumen thereof, such tubular member having its proximal end received within the distal portion of the shaft. A spring coil distally ending in a tip extends axially from the shaft and surrounds the tubular member and the shaft, the spring coil and the tubular member are soldered together at their connection areas. A solid core extends from the distal end of the tubular member within the coil, with its proximal end welded to the tubular member and its distal end welded to a disk located within the coil. A safety wire connects the disk to the tip of the coil and pressure monitoring holes are formed in the wall of the tubular extension, near the distal end thereof. Operation of this guide wire is as follows: a dilatation catheter with an inflatable balloon towards its distal end is inserted into a blood vessel through a guiding catheter and advanced into the desired artery along the guide wire which is positioned so that the pressure monitoring holes are positioned beyond the distal end of the dilatation catheter when the balloon is in position to dilate a lesion. With the balloon dilated, the pressure on the distal side of the balloon can be monitored at the proximal end of the guide wire through the pressure monitoring holes and the luminal openings in the shaft and tubular member. An adapter may be attached to the proximal end of the shaft for attachment to a stopcock manifold. If an extension wire is needed, the adapter may be removed and an extension shaft having a long tapered tip may be press-fit into the proximal end of the tubular shaft. The original catheter may then be removed and replaced with an alternate catheter. The extension wire is then removed and the adapter is replaced on the proximal end of the guide wire for pressure monitoring. U.S. Pat. No. 4,953,553 also refers to such a device.

Another approach is shown in the document EP 0 419 277 which describes a guide wire for use in measuring a characteristic of liquid flow in a vessel, comprising a flexible elongate element in the form of a tube with a core wire provided therein to provide additional rigidity and torqueability to the guide wire. The core wire extends beyond the distal end of the tube into a coil spring assembly which is soldered to the tube and to the core wire. The coil spring assembly is formed of two parts which are screwed together and the assembly is soldered to the core wire at the region where the two portions of coil are screwed together. A safety wire extends from the joint of the two coils to the distal extremity of the coil spring assembly where it is secured to a transducer carried by the distal end of the coil spring assembly. Front and rear contacts are provided on the transducer and are connected to a two conductor wire which extends rearwardly and interiorly of the coil spring assembly and further extends into the tube between the core wire and the interior of the tube to get out of the tube for connection to a male connector. According to a variant, an insulating sleeve may form a tight fit with the exterior surface of the core wire and it may also fit within the tube to insulate the core from the tube so that the core and tube may serve as separate and independent electrical conductors.

European Patent Application No. 95105777.7 filed Apr. 18, 1995, describes a pressure measuring guide wire comprising an elongated hollow shaft the proximal end of which is for connection to a pressure monitoring equipment. The distal area of the shaft comprises a plurality of elongated slots formed in the shaft wall for pressure medium entry, whereby the resistance to kinking of that area is smaller than that of the proximal area of the shaft which is devoid of slots. A coil, possibly made of a radiopaque metal, is located inside the shaft under the slots for supporting the wall and slot structure and for providing a radiopaque reference to that area. A core member is located within the coil with proximal and distal ends formed to abut longitudinally with the corresponding ends of the coil in order to stiffen the coil. In a variant, the core member may have its proximal end extended by a wire which goes proximally along and out of the lumen of the shaft. In that case, the supporting coil may be placed under the slots only for insertion of the guide wire to assure resistance to kinking, when the guide wire is properly located, the supporting coil and wired core assembly may be removed from the guide wire to maintain the shaft lumen free of obstructions for pressure measurements.

It is an object of this application to propose a medical appliance for pressure measurement in a blood vessel which is easy and inexpensive to manufacture, which has an appreciable handling versatility while providing very good qualities of resistance, steerability and pushability, and which allows a smooth advance of pressure waves in a very low profile guide wire configuration.

SUMMARY OF THE INVENTION

Accordingly, with the stiffening means consisting of an independent wire removably extending within at least a portion of the lumen and proximally of the proximal area of the shaft, it becomes possible to select a basic stiffness and floppyness for the shaft and to either withdraw the independent wire from the shaft lumen and to replace it by another independent wire having other characteristics, or to displace the independent wire along the shaft lumen. The stiffness and flexibility of the shaft as well as its resistance to kinking and floppyness are thus fully selectable and assured, and they may be modulated by the independent wire without any detriment to the selected shaft configuration or intrinsic qualities, and most of all without increasing its outer size. The shaft therefore may be devised as a mere tubing with extremely thin walls which can be safely and efficiently advanced through tortuous and narrow vessels as well as through acute stenoses. For pressure measurements, it suffices to withdraw the independent wire to take advantage of a lumen which is fully free of any obstruction, whereby a better frequency behavior for the fluid medium. And as the shaft lumen is always free of obstruction for pressure measurement, it is possible with a thin walled shaft to have a shaft with a very low profile and a relatively large lumen assuring a good flow of the fluid medium for pressure measurements.

When the independent wire is coiled, it is possible to assure the required stiffness for the shaft while having a greater elasticity for the independent wire, which may be of further help for extremely thin walled shafts.

When the independent wire has an outer transverse size which decreases from a proximal portion to a distal portion thereof, a greater modulation of stiffness and floppyness is achieved for the shaft which can be further modified by displacement of the independent wire along the lumen or its mere replacement by another wire similarly devised.

With an independent wire frictionally extending within the lumen, it is possible to achieve the lowest profile for the tubular shaft because of the closest relationship between independent wire and shaft while retaining all the other characteristics of the appliance. Simultaneously, there is the advantage that the independent wire is retained in the position chosen by the practitioner for particular shaft stiffness modulation.

Where a luer-lock is removably mounted on the shaft, the practitioner has the great advantage that he can use the pressure measurement appliance as a conventional guide wire. After insertion of the luer-lock equipped appliance proximally and distally of a stenosis for determining the pressure gradient, it suffices to remove the luer-lock for inserting a catheter such as a balloon catheter over the appliance which then acts as a pure guide wire which is already in place for guiding the balloon catheter exactly at the place required. Time and cost saving is achieved and extra manipulations for inserting a new guide wire after pressure measurement and withdrawal of the pressure measuring device are avoided while maintaining all the advantages of the appliance which becomes an efficient and low profile purpose device.

When abutment means on the independent wire are securing an end position of the independent wire in the lumen, the practitioner may simply insert the independent wire into the shaft without particular precautions as to its longitudinal position within the lumen, knowing that the independent wire will not go beyond a pre-fixed position in the lumen. He can also use that pre-fixed position as a reference for further modulation of the shaft stiffness by displacement in the independent wire.

In sum, the present invention relates to a medical appliance for pressure measurement in a blood vessel. It has an elongated flexible shaft with a proximal area and a distal area, a lumen extending through the shaft from the proximal area to the distal area thereof, aperture means in the distal area of the shaft for the entry of a pressure medium into the lumen, and stiffening means in the lumen for stiffening shaft portions with full available shaft stiffness. The stiffening means may be an independent wire removably extending within at least a portion of the lumen and proximally of the proximal area of the shaft. The independent wire may be coiled, and may have an outer transverse size which decreases from a proximal portion to a distal portion thereof. The independent wire may frictionally extend with the lumen. The medical appliance may have a luer-lock removably mounted on the shaft. Abutment means on the independent wire may secure an end position of the independent wire in the lumen.

DESCRIPTION OF THE DRAWINGS

These and other objects, features and advantages of the invention will become readily apparent from the following detailed description with reference to the accompanying drawing which shows, diagrammatically and by way of example only, preferred but still illustrative embodiments of the invention.

DESCRIPTION OF PREFERRED EMBODIMENTS

Figure 1:
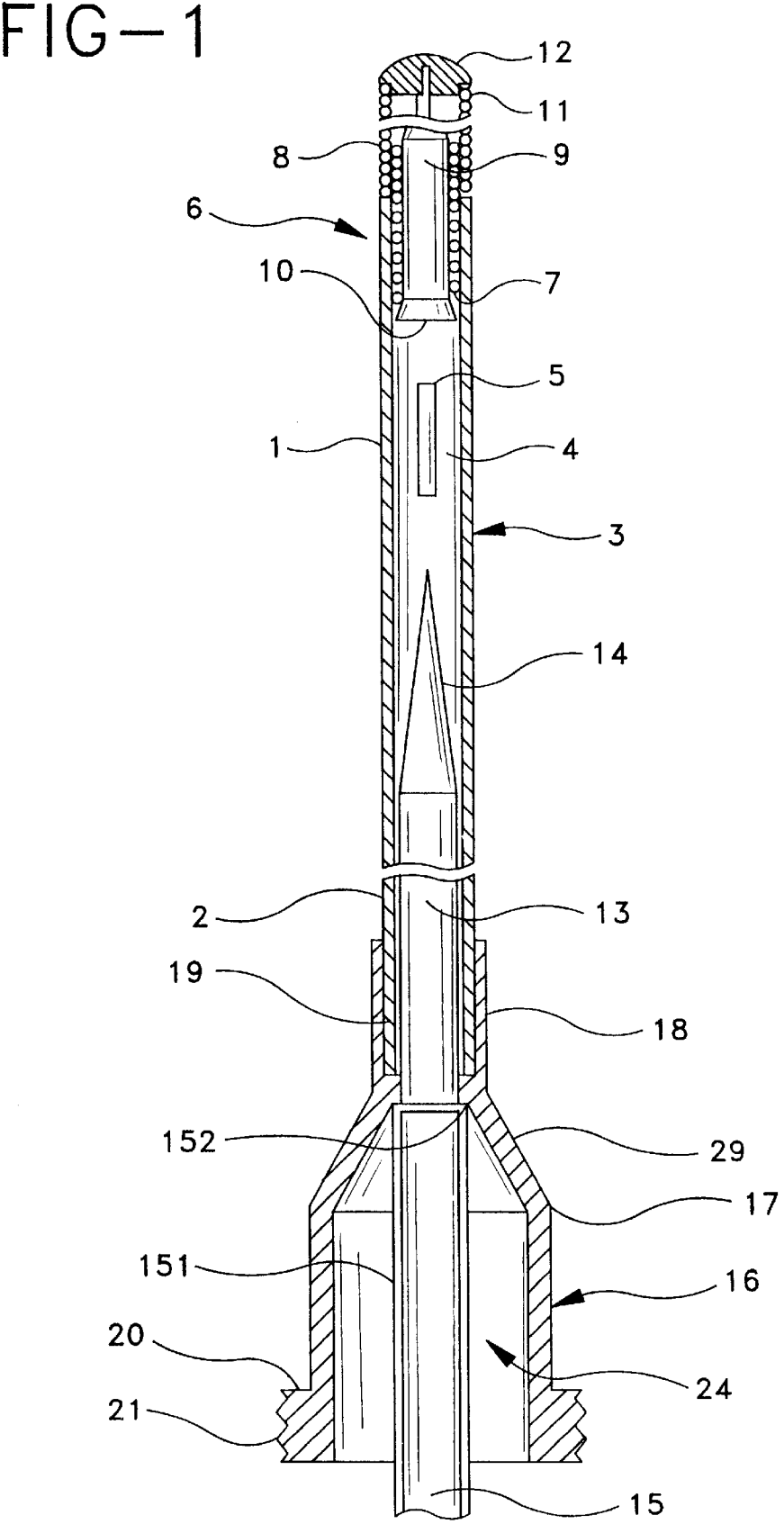
FIG. 1 is a cross sectional view of a first embodiment of the appliance according to the invention.

The appliance shown in FIG. 1 comprises an elongated shaft 1 for pressure measurement in a blood vessel, having a proximal area 2 and a distal area 3. Preferably, this shaft is made of a highly flexible material such as for instance Nitinol™ or Tinel Alloy™. Other materials are possible, such as for example plastic materials.

As shown, the shaft 1 is tubular, with a lumen 4 extending therethrough from the proximal area 2 to the distal area 3. Aperture means in the form of slots 5 are devised in the distal area 3 of the shaft 1, for the entry of the pressure medium into the lumen 4.

The distal area 3 of the shaft 1 may terminate in a flexible assembly 6 as described in the European Patent Application No. 95103006.3 filed Mar. 2, 1995, comprising a first coil 7 the proximal windings of which are spaced apart and threadedly force fitted into the distal area 3 of the shaft 1, and a second coil 8 the proximal portion of which is threadingly surrounding the distal area of first coil 7 and abutting against the distal end of the shaft 1. The first and second coils 7 and 8 may be made of a high density metal such as tungsten to provide a radiopaque reference for the flexible assembly 6. A cylindrical core 9, preferably of stainless steel, extends through the coils 7 and 8; its proximal portion 10 is flattened to abut longitudinally against the proximal end of coil 7, and its distal area tapers into a narrow portion 11 which terminates into a weld tip 12 resting against the distal end of the coil 8. However, other termination configurations are also possible.

A stiffening means formed by an independent wire 13 removably extends through lumen 4, with a tapering end 14 located in the distal area 3 of shaft 1, proximally of slots 5. The independent wire 13 extends at 15 proximally of the proximal area 2 of shaft 1 and it has a larger diameter portion 151 in that area. Such an independent wire 13 may be made, for example, of stainless steel. As shown, the independent wire 13 is frictionally mounted within lumen 4 whereby it may be displaced through the lumen in addition to be removable therefrom.

The proximal area 2 of shaft 1 is affixed into a luer-lock 16 which is adapted to be connected to a pressure measuring equipment (not shown). The luer-lock 16 may also be connected to a fluid supply equipment (not shown) as conventionally used in the art for flushing drugs through the lumen 4 and to remove occlusions of the slots 5 to assure a good pressure transition from the blood vessel (not shown) to the lumen 4, or to remove bubbles inside the lumen.

The luer-lock 16 comprises a housing 17 having an inner cavity 24 and a distal end which tapers at 29 to form a coupling muff 18 tightly sealed, for instance by glue, on the proximal end 19 of proximal area 2 of shaft 1; the proximal end of housing 17 comprises a collar 20 with an external thread 21. The proximal end 15 of independent wire 13 extends through the inner cavity 24 of the housing 17 and up to a transverse wall 152 of inner cavity 24 against which abuts the enlarged portion 151 of the independent wire 13.

Figure 2:
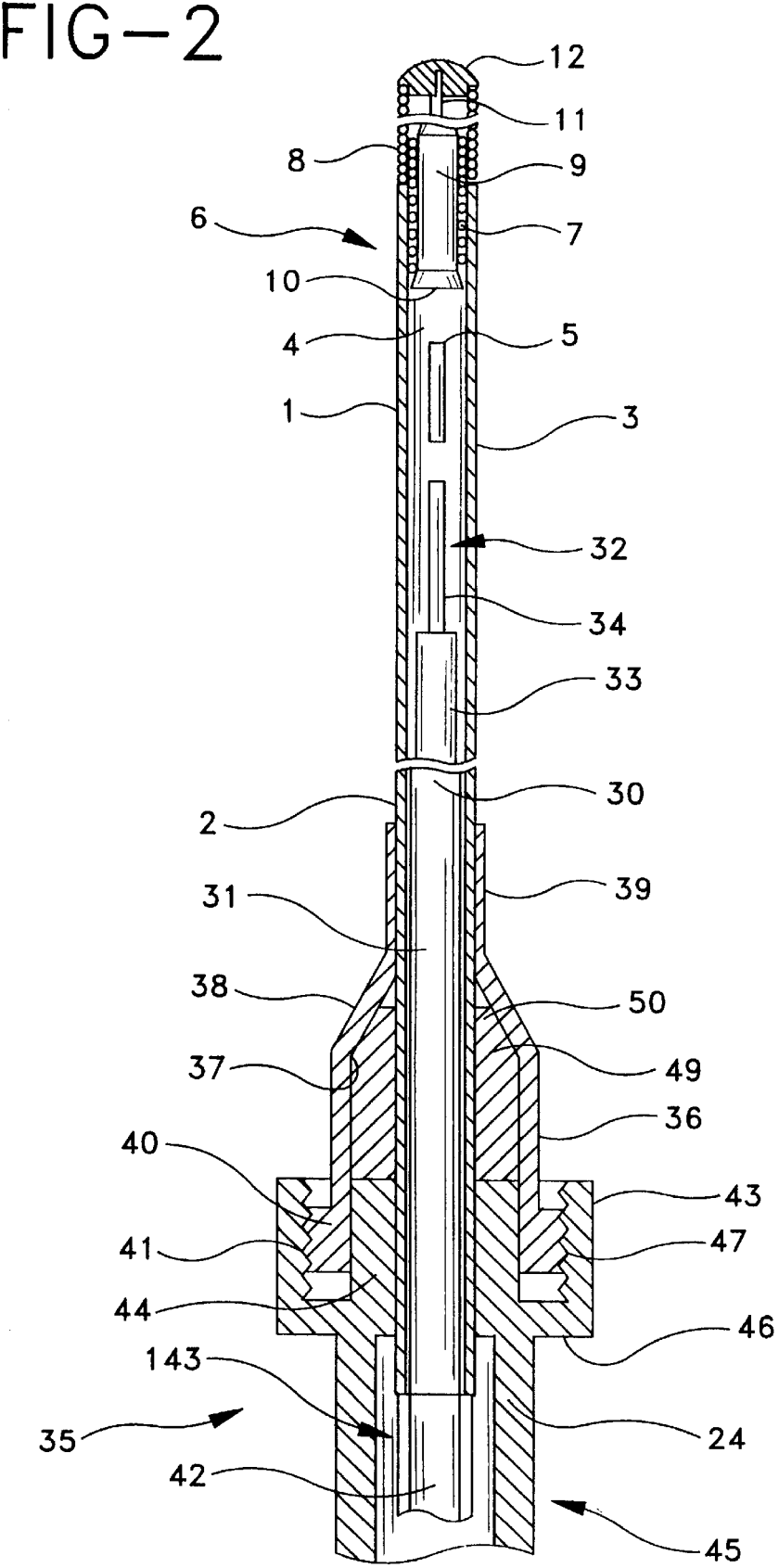
FIG. 2 is a cross sectional view of a second embodiment of the appliance.

The second embodiment shown in FIG. 2 comprises the same integers as the first embodiment for the shaft 1 and its distal area 3 terminating into a flexible assembly 6 and reference is made to the corresponding description in relation to FIG. 1.

A stiffening means formed by an independent wire 30 removably extends through lumen 4. This wire 30 also has an outer transverse size which decreases from its proximal area 31 to its distal area 32; instead of the tapering shown for the embodiment of FIG. 1, the wire has however a stepwise diameter reduction as shown at 33 and 34, the last reduced diameter section 34 being located in the distal area 3 of shaft 1, proximally of slots 5. The independent wire 30 extends at 42 proximally of the proximal area 2 of shaft 1 and it has a larger diameter portion 143 in that area abutting against the proximal end of the shaft 1. This wire may also be made of stainless steel and, as shown, it is frictionally mounted within lumen 4 for displacement therein and removal therefrom.

The proximal area 2 of shaft 1 is removably mounted into a removable luer-lock assembly 35 which is also adapted to be connected to a pressure measuring equipment or fluid supply equipment as explained in connection with the first embodiment.

The luer-lock assembly 35 comprises a first housing 36 having an inner cavity 37 and a distal end which tapers at 38 to form a muff 39 surrounding a portion of the proximal area 2 of shaft 1; the proximal end of housing 36 comprises a collar 40 with an external thread 41. The proximal area 31 of independent wire 30 together with the proximal area 2 of shaft 1 extend through the inner cavity 37 of first housing 36, with the proximal end 42 of wire 30 extending proximally of proximal area 2 of shaft 1. A second housing 43 is mounted on first housing 36 with an inner member 44 extending in the inner cavity 37 of first housing 36 and around the shaft 1. The proximal end 45 of second housing 43 is for connection to a pressure measuring equipment or fluid supply equipment (not shown) and it comprises an outer collar 46 with an inner thread 47 meshing into thread 41 of the first housing 36. Between the inner member 44 of second housing 43 and the taper portion 38 of first housing 36, a sealing member 49 with a distal taper 50 is located in the inner cavity 37, such a sealing member 49 also surrounding the shaft 1.

By this assembly, when the second housing 43 is screwed on the first housing 36, the inner member 44 is forced against sealing member 49 so that its distal taper 50 is forced against taper 38 of inner cavity 37 thereby assuring tight sealing of the assembly. Release of the second housing 43 frees the engagement of sealing member 49 from inner cavity 37 and allows full removal of the complete luer-lock assembly 35.

Figure 3:
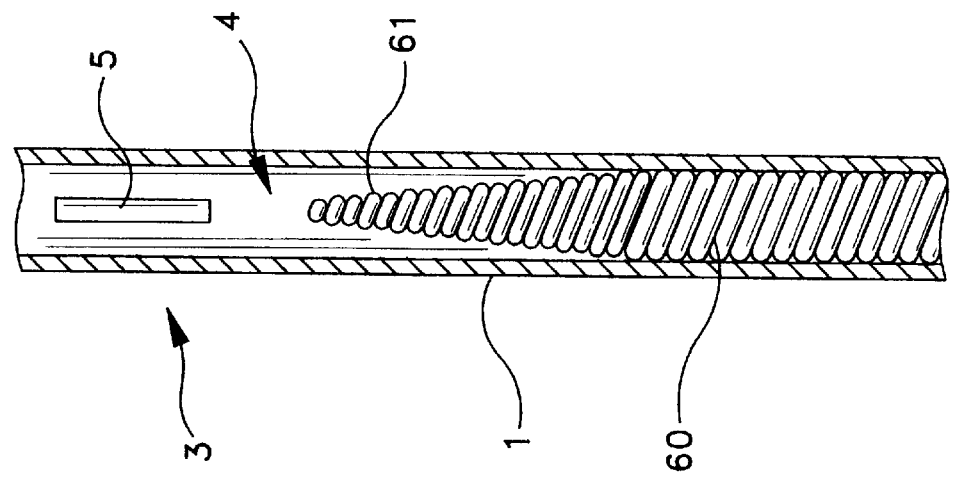
FIG. 3 is a part cross sectional view of a third embodiment of the appliance.

The third embodiment partly shown in FIG. 3 differs from the embodiments of FIG. 1 or FIG. 2 in that the independent wire 60 is a coiled wire removably extending through lumen 4, with a tapering end 61 located in the distal area of shaft 1, proximally of slots 5. Such an independent wire 60 may also be made of stainless steel and, as shown, it is frictionally extending within the lumen 4 whereby it may also be displaced through the lumen in addition to be removable therefrom.

Figure 4:
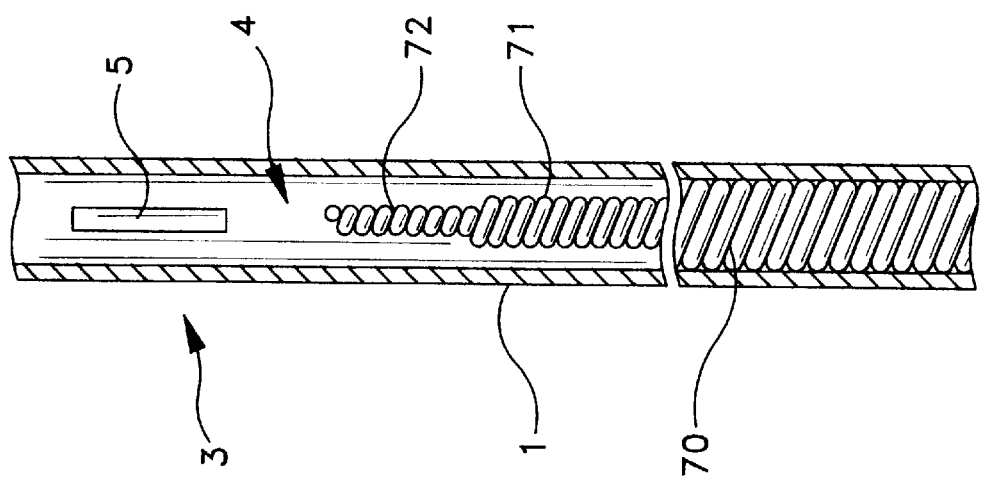
FIG. 4 is a part cross sectional view of a fourth embodiment of the appliance.

The fourth embodiment partly shown in FIG. 4 differs from the embodiments of FIG. 1 or FIG. 2 in that the independent wire 70 is made of a coil which has a stepwise outer diameter size reduction as shown at 71 and 72, the last reduced diameter section 72 being located in the distal area 3 of shaft 1, proximally of slots 5. As for the other embodiments, this wire may be made of stainless steel and, as shown, it is frictionally mounted within lumen 4 for displacement therein and removal therefrom.

Variants are available without departing from the scope of the invention. For instance, instead of having an outer transverse size which decreases from a proximal portion to a distal portion, the independent wire may have an outer transverse size which remains unchanged from a proximal portion to a distal portion of the independent wire. Instead of frictionally extending within the lumen, the independent wire may have an outer transverse size which is somewhat smaller than the inner transverse size of the lumen. The independent wire may also be made of a plastic material. The shaft 1 may be made of plastic material as indicated hereinbefore as well as it may be made of a compound structure of a plastic material surrounded by a thin coil of metal, or still solely of a coil of metal. And of course, the structures on either the fixed luer-lock configuration of FIG. 1 or the removable luer-lock assembly of FIG. 2 may be replaced by other luer-lock configurations, fixed or removable, to the extent that they perform the same function. Also, the enlarged diameter abutment at 151 or 143 securing the end position of the stiffening wire in the lumen 4 may be replaced by other configurations such as, for instance, studs in the independent wire.

What is claimed is:

1. An elongate medical device for pressure measurement in a blood vessel comprising:
   an elongate flexible tube having a stiffness and a lumen therein for transmitting a pressure wave from an at least one distal opening in the elongate tube to a proximal opening in the elongate tube;
   a luer-lock assembly removably mounted to a proximal end of the elongate tube, the luer-lock assembly configured to be removed from the elongate flexible tube so that a balloon catheter or other medical device may be advanced over the elongate tube and to a vascular treatment site, the luer-lock assembly comprising;
      a first housing having an inner cavity, a distal end which tapers to form a muff, the muff configured to surround a proximal portion of the elongate tube, and a proximal end comprising a collar having an external thread;
      a second housing mounted on the first housing and having a proximal end comprising an outer collar with an inner thread for threaded connection to the proximal end of the first housing and further configured for connection to a pressure measuring device or a fluid supply system; and
      a sealing member positioned in the inner cavity of the first housing, the sealing member configured to seal around the elongate member when the first housing is threadedly engaged with the second housing; and
   an elongate stiffening member configured to be removably inserted into the elongate tube for varying the stiffness of the elongate tube.

2. The elongate medical device for pressure measurement in a blood vessel of claim 1 wherein the elongate stiffening member is formed from a material from the group consisting of stainless steels, nickel-titanium alloys, polymers and a composite of polymers and metallic alloys.

3. The elongate medical device for pressure measurement in a blood vessel of claim 1 wherein the elongate stiffening member comprises an elongate coil of wire.

4. The elongate medical device for pressure measurement in a blood vessel of claim 3 wherein the elongate coil varies in diameter to change a stiffness profile of the elongate stiffening member.

5. The elongate medical device for pressure measurement in a blood vessel of claim 1 wherein the elongate stiffening member varies in stiffness along its length.

6. The elongate medical device for pressure measurement in a blood vessel of claim 1 wherein the elongate stiffening member further comprises an abutment means near a proximal end of the stiffening member, the abutment means preventing the stiffening member from being inserted beyond a certain point in the flexible tube.

7. The elongate medical device for pressure measurement in a blood vessel of claim 1 wherein the elongate stiffening member further comprises a tapered distal end configured to facilitate insertion of the stiffening member into the flexible tube.

8. The elongate medical device for pressure measurement in a blood vessel of claim 1 further comprising a flexible assembly attached to a distal end of the elongate tube and configured to reduce any trauma to the vasculature.

9. A medical device for intravascular blood pressure measurement comprising:
   an elongate flexible tube having a stiffness and a lumen therein for transmitting a pressure wave from an at least one distal opening in the elongate tube to a proximal opening in the elongate tube;
   an elongate stiffening member configured to be removably inserted into the elongate tube for varying the stiffness of the elongate tube; and
   a removable means for coupling the tube to the stiffening member, the removable means comprising a means for housing a sealing member, the sealing member positioned in the housing means such that the sealing member seals around the elongate tube.

10. The medical device for intravascular blood pressure measurement of claim 9 wherein the elongate stiffening member is formed from a material from the group consisting of stainless steels, nickel-titanium alloys, polymers and a composite of polymers and metallic alloys.

11. The medical device for intravascular blood pressure measurement of claim 9 wherein the elongate stiffening member comprises an elongate coil of wire.

12. The medical device for intravascular blood pressure measurement of claim 9 wherein the elongate coil varies in diameter to change a stiffness profile of the elongate stiffening member.

13. The medical device for intravascular blood pressure measurement of claim 9 wherein the elongate stiffening member varies in stiffness along its length.

14. The medical device for intravascular blood pressure measurement of claim 9 wherein the elongate stiffening member further comprises an abutment means near a proximal end of the stiffening member, the abutment means preventing the stiffening member from being inserted beyond a certain point in the flexible tube.

15. The medical device for intravascular blood pressure measurement of claim 9 wherein the elongate stiffening member further comprising a tapered distal end configured to facilitate insertion of the stiffening member into the flexible tube.

16. The medical device for intravascular blood pressure measurement of claim 9 further comprising a flexible assembly attached to a distal end of the elongate tube and configured to reduce any trauma to the vasculature.

17. The elongate medical device for pressure measurement in a blood vessel of claim 9 wherein the removable means for coupling the tube to the stiffening member comprises:
   a first housing having an inner cavity, a distal end which tapers to form a muff, the muff configured to surround a proximal portion of the elongate tube, and a proximal end comprising a collar having an external thread;
   a second housing mounted on the first housing and having a proximal end comprising an outer collar with an inner thread for threaded connection to the proximal end of the first housing and further configured for connection to a pressure measuring device or a fluid supply system; and
   a means for sealing about the elongate tube when the first housing is engaged with the second housing.

18. An elongate medical device for pressure measurement in a blood vessel comprising:

an elongate flexible tube having a proximal area, a distal area, a lumen extending through the tube from the proximal area to the distal area, and aperture means in the distal area of elongate tube to a proximal opening in the elongate tube; and a luer-lock assembly removably mounted to a proximal end of the elongate tube, the luer-lock assembly configured to be removed from the elongate flexible tube so that a balloon catheter or other medical device may be advanced over the elongate tube and to a vascular treatment site and comprising;
 a first housing having an inner cavity, a distal end which tapers to form a muff, the muff configured to surround a proximal portion of the elongate tube, and a proximal end comprising a collar having an external thread;
 a second housing mounted on the first housing and having a proximal end comprising an outer collar with an inner thread for threaded connection to the proximal end of the first housing and further configured for connection to a pressure measuring device or a fluid supply system; and
 a sealing member positioned in the inner cavity of the first housing, the sealing member configured to seal around the elongate tube when the first housing is threadedly engaged with the second housing.

19. The elongate medical device for pressure measurement in a blood vessel of claim 18 wherein the elongate tube is formed from a material from the group consisting of stainless steels, nickel-titanium alloys, polymers and a composite of polymers and metallic alloys.

20. The elongate medical device for pressure measurement in a blood vessel of claim 18 further comprising a flexible assembly attached to a distal end of the elongate tube and configured to reduce any trauma to the vasculature.

* * * * *